US00RE36247E

United States Patent [19]

Plunkett et al.

[11] E Patent Number: Re. 36,247

[45] Reissued Date of Patent: Jul. 6, 1999

[54] METHOD OF HORMONAL TREATMENT FOR MENOPAUSAL OR POST-MENOPAUSAL DISORDERS INVOLVING CONTINUOUS ADMINISTRATION OF PROGESTOGENS AND ESTROGENS

[75] Inventors: Earl E. Plunkett; Bernard M. J. Wolfe, both of London, Canada

[73] Assignees: WOCO Investments, Ltd.; Pre JAY Holdings, Limited, both of Canada

[21] Appl. No.: 08/542,941

[22] Filed: Oct. 13, 1995

Related U.S. Patent Documents

Reissue of:

[64] Patent No.: 4,826,831
Issued: May 2, 1989
Appl. No.: 06/635,236
Filed: Jul. 24, 1984

U.S. Applications:

[63] Continuation-in-part of application No. 06/520,834, Aug. 5, 1983, abandoned.

[51] Int. Cl.[6] ..... A61K 31/56

[52] U.S. Cl. ..... 514/170

[58] Field of Search ..... 514/170

[56] References Cited

U.S. PATENT DOCUMENTS

| | | | |
|---|---|---|---|
| 3,639,600 | 2/1972 | Hendrix . | |
| 3,733,407 | 5/1973 | Segre . | |
| 3,836,651 | 9/1974 | Rudel et al. | 514/170 |
| 3,957,982 | 5/1976 | Lachnit-Fixson et al. | 514/170 |
| 4,018,919 | 4/1977 | Black . | |
| 4,425,339 | 1/1984 | Pitchford | 514/170 |

FOREIGN PATENT DOCUMENTS

| | | |
|---|---|---|
| OS 2645307 | of 0000 | Germany . |
| 1578340 | 11/1980 | United Kingdom . |
| 2096462 | 10/1982 | United Kingdom . |

OTHER PUBLICATIONS

*Acta Obstet. Gynecol. Sand.*, 59, 327–329 (1980) [Mugglestone].

Abstract—Paper delivered by Dr. Magos to the 23rd British Congress on the Menopause, Royal College of Obstetrics and Gynecology, Birmingham, Jul. 1983 [Magos].

1984 Physicians' Desk Reference (PDR) pp. 222, 545, 658, 1205, 1513 and 2044.

*Maturitas*, 3, 145–156 (1981) [Staland].

English translation of Plunkett's Oct. 28, 1993 reply in an opposition proceeding in the Danish patent application [Danish Patent Application No. 3770/84 (165,390)] equivalent to Plunkett.

*FASS*, 459 (Mar. 1984) (Pharmaceutical Specialties in Sweden) [Sweden].

English translation of, *FASS*, 459 (Mar. 1984) (Pharmaceutical Specialities in Sweden) [Sweden], item (A).

*Minerva Ginecologica*, 21(4), 193–7 (1969) [GOISIS].

English translation of *Minerva Ginecologica*, 21(4), 193–7 (1969) [GOISIS], item (C).

*Aust. N. Z. J. Obstet. Gynaec.*, 23, 43 (1983) [Smith].

*Report from Workshop*, 157–165 (Aug. 1982)—Socialstyrelsens komitte' for lakemedelsinformation, workshop, Menopaus Substitutionsbehandling med ostrogen, Aug. 30–31, 1982 (published Jan. 1983) [Workshop report].

English translation of, *Report from Workshop*, 157–165 (Aug. 1982)—Socialstyrelsens komitte' for lakemedelsinformation, workshop, Menopaus Substitutionsbehandling med ostrogen, Aug. 30–31, 1982 (published Jan. 1983) [Workshop Report], item (F).

Novo Nordisk's Supplementary Opposition Statement filed Jul. 16, 1997 in Danish Patent Application No. 3770/84.

English translation of, Novo Nordisk's Supplementary Opposition Statement filed Jul. 16, 1997 in Danish Patent Application No. 3770/84, item (H).

Applicants' Agents' Request for Revival and Comments filed Nov. 15, 1996 in Danish Patent Application No. 3770/84 (165,390).

English translation of, Applicants' Agents' Request for Revival and Comments filed Nov. 15, 1996, item (J).

Declaration of Dr. Adam L. Magos signed Jun. 5, 1997.

Declaration of Ms. Caroline B. Roney signed June. 10, 1997.

Mugglestone et al., "Combined Estrogen and Progestogen For The Menopause", Acta Obstet. Gynecol. Scand. 59:327–329, 1980.

Magos et al., 23rd British Congress, Royal College of Obstetrics and Gynecology, Birmingham, p. 156, Jul. 1993.

Chemical Abstracts, vol. 83, No. 9, Sep. 1, 1975, p. 142, Abstract No. 725288.

Novo Industri AB, "Kliogest®: Ostrogenpreparat med gestagentillsats" Mar. 1984 (Translation provided).

Eiken, P., N. Kolthoff and S. Pors Nielsen, "Ten Years Effects of Hormonal Replacement Therapy On Bone Mineral Content in Post-Menopausal Women," Department of Clinical Physiology, Hillerod Hospital, DK-3400 Hillerod, Denmark (1996).

(List continued on next page.)

*Primary Examiner*—Raymond J. Henley, III

*Attorney, Agent, or Firm*—Pillsbury Madison & Sutro LLP

[57] ABSTRACT

A method of hormonally treating menopausal (including perimenopausal and post-menopausal) disorders in women, a composition, and a multi-preparation pack therefor. The administrative regimen to which the pack is particularly adapted comprises continuously and uninterruptedly administering a progestogen to a woman while cyclically administering an estrogen by using a repetitive dosage regimen. This regimen calls for administering the estrogen continuously for a period of time between about 20 and about 120 days, followed by terminating administering the estrogen for a period of time between about 3 and about 7 days. Alternatively, both the progestogen and estrogen may be administered for the full treatment period without interruption. The regimen avoids many of the problems associated with the administration of estrogen alone or with progestogen administered according to conventional regimens, and also avoids problems associated with such conventional regimens by maintaining the estrogen and progestogen at low daily dosage levels of between 0.005 mg and 2.5 mg estrogen and 0.25 mg and 30 mg progestogen.

46 Claims, 1 Drawing Sheet

OTHER PUBLICATIONS

Eiken, P., N. Kolthoff, S. Pors Nielsen and O. Barenholdt, "Eight Years Effects of Hormonal Replacement Therapy on Mineral Content in Post–Menopausal Women," Department of Clinical Physiology and Nuclear Medicine, Hillerod Sygebus, Helsevej 2, DK–3400 Hillerod (1995).

Eiken, P. and N. Kolthoff, "Compliance with long–term oral hormonal replacement therapy," Maturitas, vol. 22: 97–103, Sep. 1995.

Goisis M. "Treatment of Pre–climacteric and Climacteric introducing a New Estrogen–progestin Association" Minerva Ginecologica, 21 pages 193–197 (1969).

Lakartidningen, vol. 81, No. 12, Mar. 21, 1984 (translation provided).

Madsen V., Postmenopausal Estrogen Treatment, Manedsskrift for Praktisk Laegegering, vol. 45 (8) 1967 (translation provided).

Magos AL, et al "Amenorrhea and Endometrial Atrophy with Continuous Oral Estrogen and Progestogen Therapy in Post–Menopausal Women", *Obstet. gynecol 65:*496 (1985).

Maschak CA, et al "Comparison of pharmaceodynamic properties of various estrogen formulations", *Am. J. Obstet. Gynecol.* 144:51 (1982).

Smith M, et al, "A Double–Blind Trial of Ethinyloestradio and Norethisterone Separately and Together, in Menopausal Women", *Aust. N.Z. J. Obstet. Gynaec.* 23: 43 (1983).

Workshop, Menopause, Substitutional Treatment with Estrogen, Socialstyrelsens Kommittee for lakemedelsinformation, 1983 (translation provided).

Mann JI, Vessey MP, Thorogood M, Doll R, Myocardial infarction in young women with special reference to oral contraceptive practice, *Brit Med J* 1975;2:241–245.

Mattsson L–Å, Samsioe G, Estrogen–progestogen replacement in climacteric women, particularly as regards a new type of continuous regimen, *Acta Obstet Gynecol Scand Suppl* 1985;130:53–58.

Plunkett ER, Contraceptive steroids, age, and the cardiovascular system, *Am J Obstet Gynecol* 1982;142:747–751.

Stolley PD, Tonascia JA, Tockman MS, et al, Thrombosis with low–estrogen oral contraceptives, *Am J Epidemiol* 1975;102:197–208.

Silfverstolpe G, Gustafson A, Samsioe G, Svanborg A, Lipid metabolic studies in oophorectomized women: effects induced by two different estrogens on serum lipids and lipoproteins, *Gynecol obstet Invest* 1980;11:161–169.

Tietze C, Lewit S, Life risks associated with reversible methods of fertility regulation, *Int J Gynaecol Obstet* 1979;16:456–459.

Heiss G, Tamir I, Davis CE, et al., Lipoprotein–cholesterol distributions in selected North American population: The Lipid Research Clinics Program Prevalence Study, *Circulation,* 1980;61:302–315.

Hiryonen E, Mälkönen M, Mannien V, Effects of different progestogens on lipoproteins during postmenopausal replacement therapy, *N Engl J Med,* 1081;304:560–563 (1981).

Kay CR, The happiness pill? *J Roy Coll Gen Pract,* 1980;30:8–19.

Khoo SK, Hacker N, Chang A, An incremental–dose combined oestrogen–progestogen oral contraceptive: effects on body weight, blood pressure, and biochemical parameters, *Aust N Z J Obstet Gynaec,* 1980;20:1712–176.

Larsson–Cohn U, Fähraeus L, Wallentin L, Zador G, Lipoprotein changes may be minimized by proper composition of a combined oral contraceptive, *Fertil Steril,* 1981;35:172–179.

Mann JI, Inman WHW, Oral contraceptives and death from myocardial infarction, *Brit Med J,* 1975;2:245–248.

Staland B, Continuous Treatment with Natural Oestrogens and Progestogens, A Method to Avoid Endometrial Stimulation, *Maturitas* 1981;3:145–156.

Mattsson L–Å, Callberg G, Samsioe G, Evaluation of a Continuous oestrogen–progestogen regimen for climacteric complaints, *Maturitas* 1982;4:95–102.

Bloch B., The effect of cyclical administration of levonorgestrel and ethinyloestradiol on blood pressure, body mass, blood glucose and serum triglycerides, *S Afr Med J* 1979;56:568–570.

Boston Collaborative Drug Surveillance Program, Boston University Medical Center, Surgically confirmed gallbladder disease, venous thromboembolism and breast tumors in relation to postmenopausal estrogen therapy, *N Engl J Med* 1974;290:15–19

Collaborative Group for the Study of Stroke in Young Men, Oral contraception and increased risk of cerebral ischemia or thrombosis, *N Engl J Med* 1973;288:871–878.

Gambrell RD Jr, Maier RC, Sanders BI, Decreased incidence of breast cancer in postmenopausal estrogen–progestogen users, *Obstet Gynecol* 1983;62:435–443.

Gambrell RD Jr, Bagnell CA, Greenblatt RB, Role of estrogens and progesterone in the etiology and prevention of endometrial cancer: review, *Am J Obstet Gynecol* 1983;146:696–707.

Gordon T, Castelli WP, Hjortland MC, Kannel WB, The prediction of coronary heart disease by high–density and other lipoproteins: an historical perspective, In:Rifkind BM, (1977).

Archer, D.F. et al., Bleeding Patterns in Postmenopausal Women Taking Continuous Combined or Sequential Regimens of Conjugated Estrogens With Medroxyprogesterone Acetate, Obstet. Gynecol., Vo. 83, No. 5, pp. 686–692 (May 1994) (E14).

Bewtra, Chhanda et al., Endometrial Histology and Bleeding Patterns in Menopausal Women Treated With Estrogen and Continuous Cyclic Progestin, J. Reproductive Med., vol. 33, No. 2, pp. 205–208 (Feb. 1988) (E10).

Brosens, I.A. et al., Assessment of Incremental Dosage Regimen of Combined Estrogen–Progestogen Oral Contraceptives, Br. Med. J., vol. 4(5945), pp. 643–645 (1974) (P56).

Christiansen, C.et al., Does Oestriol Add to the Beneficial Effect of Combined Hormonal Prophylaxis Against Early Postmenopausal Osteoporosis, Brit. J. Obstet. Gynaecol., vol. 91, pp. 489–493 (May 1984) (P45).

Clark, James H. et al., Nuclear Binding and Retention of the Receptor Estrogen Complex: Relation to the Agnostic and Antagonistic Properties of Estriol, Endo, vol. 1, No. 1, pp. 91–96 (1977) (P27).

Clisham, P. Ronald et al., Comparison of Continuous Versus Sequential Estrogen and Progestin Therapy in Postmenopausal Women, Obstet. Gynecol., vol. 77, No. 2, pp. 241–242 (Feb. 1991) (E9).

Dennerstein, Lorraine et al., Menopausal Hot Flushes: A Double Blind Comparison of Placebo, Ethinyl Oestradiol and Norgestrel, Brit.J. Obstet. Gynecol., vol. 85, pp. 852–856 (Nov. 1978) (P31).

Dennerstein, Lorraine et al, Hormone Therapy and Affect, Maturitas, vol. 1, pp. 247–259 (1979) (P31a).

Dennerstein, Lorraine et al., Plasma Levels of Ethinyl Oestradiol and Norgestrel During Hormone Replacement Therapy, Maturitas, vol. 2, pp. 147–154 (1980) (P32).

Dickey, Richard P. & Stone, Sergio C., Progestational Potency of Oral Contraceptives, Obstet. Gynecol., vol. 47, No. 1, pp. 106–112 (Jan. 1976) (P9).

Dickey, Richard P., Reply to Paper by Dr. Edgren on "Progestational Potency of Oral Contraceptives: a Polemic", Int. J. Fertil., vol. 23(3), pp. 170–174 (1978) (P11).

Edgren, Richard A., Progestational Potency of Oral Contraceptives: a Polemic, Int. J. Fertil., vol. 23(3), pp. 162–169 (1978) (P10).

Eizemann, U et al., Abstract: Continuous Treatment of Menopausal Symptoms with an Estrogen/Progestogen Combinations. Results of a Multicenter Trial, J. Steroid. Biochem., vol. 17, No. 3, 1982, p. 306 (6th International Congress on Hormonal Steroids, Jerusalem, Israel, Sep. 5–10, 1982) (P36).

Englund, D.E. & Johansson, E.D.B., Endometrial Effect of Oral Estriol Treatment in Postmenopausal Women, Acta Obstet. Gynecol. Scand, vol. 59, pp. 449–451 (1980) (P26).

Hammond, Charles B. et al., Effects of Long Term Estrogen Replacement Therapy, Am. J. Obstet. Gynecol, vol. 133, No. 5, pp. 537–547 (Mar. 1, 1979) (P17).

Hellberg, D. & Nilsson, S., Comparison of Triphasic Oestradiol/Norethisterone Acetate Preparation With and Without Oestriol Component in the Treatment of Climacteric Complaints, Maturitas, Vol 5, pp. 233–243 (1984) (P44).

Hillard, T.C. et al., Continuous Combined Conjugated Equine Estrogen–Progestogen Therapy: Effects of Medroxyprogesterone Acetate and Norethindrone Acetate on Bleeding Patterns and Endometrial Histologic Diagnosis, Am J. Obstet. Gynecol., vol. 167, No. 1, pp. 1–7 (Jul. 1992) (E8).

Johansson, Elof D.B., Ostrogena Och Gestagena Substansers Effekter Pa Tumorer I Reproduktionsorganen (The Effects of Estrogenic and Gestagenic Substances on Tumours in the Reproductory Organs), Report from Workshop: Menopaus, pp. 129–141 (1982) [with translation] (Part of P2).

Johansson, Elof D.B., Nagra Utvecklingslinjer Kring Substitutions–Behandling Efter Menopaus (A few Courses of Development for the Substitution Treatment After Menopause), Report from Workshop: Menopaus, pp. 157–164 (1982) [with translation] (Part of P2).

King, Roger J.B. & Whitehead, Malcom I., Assessment of the Potency of Orally Administered Progestins in Women, Fertility & Sterility, vol. 48, No. 6, pp. 1062–1066 (Dec. 1986) (E19).

Lacey, R.W. et al., Safety of Progestins: Effects of Dydrogesterone on Blood Lipids, Br. J. Clin. Pract. Suppl. 24, pp. 4–10 (1983) (P23).

Levrant, Seth G. & Barnes, Randall B., Pharmacology of Estrogens, in Treatment of Postmenopausal Women: Basic and Clinical Aspects, ch. 6, pp. 57–67 (Rogerio A. Lobo ed., 1994) (E27).

Lillienberg, L. et al., Effect of a Sequential Oestrogen–Progestin Therapy on the Plasma Level of Oestrogens and Lipids in Post–Menopausal Women, Acta Endocrinologica, vol. 92, pp. 319–329 (1979) (P21).

Luciano, Anthony Adolph et al., Clinical and Metabolic Responses of Menopausal Women to Sequential Versus Continuous Estrogen and Progestin Replacement Therapy, Obstet. Gynecol., vol. 71, No. 1, pp. 39–43 (Jan. 1988) (E11).

Luciano, Anthony A. et al., Evaluation of Low–Dose Estrogen and Progestin Therapy in Postmenopausal Women, J. Reproductive Med., vol. 38, No. 3, pp. 207–214 (Mar. 1993) (E7).

Magos, A.L., Endometrial and Menopausal Response to Continuous Oestrogen Progestogen Therapy in Post–Menopausal Women, Summary of Paper to be Presented at Advances in the Management of Menopause Symposium on Friday, 9th Dec., 1983 (P28).

Mattsson, L.–A. et al., Effects of a Continuous Estrogen–Progestogen Therapy for Climacteric Symptoms on Circulating Sex Steroids and Gonadotrophins, Arch. Gynecol., vol. 233, pp. 101–107 (1983) (P41).

Merck, pp. CI278, CI102, 454, 3648–49, 3654–55 (1983) (P34).

Merck, p. 493 (1989) (E23).

Nand, S.L. et al., Continuous Combined Piperazine Oestrone Sulphate and Medroxyprogesterone Acetate Hormone Replacement Therapy—A Study of Bleeding Pattern, Endometrial Response, Serum Lipid and Bone Density Changes, Aust. and N.Z. J. Obstet. Gynaecol., pp. 92–96 (1995) (E6).

Neumann, Von F. et al., Probleme der Dosisfindung: Sexualhormone, Drug. Res., pp. 296–318 (1977) (P20).

Neumann, F., The physiological Action of Progesterone and the Pharmacological Effects of Progestogens—a Short Review, Postgraduate Med. J., vol. 54 (Suppl. 2), pp. 11–24 (1978) (P48).

Notelovitz, Morris et al., Oestrogen–Progestin Therapy and the Lipid Balance of Post–Menopausal Women, Maturitas, vol. 4, pp. 301–308 (1982) (P47).

Notelovitz, Morris et al., Combination Estrogen and Progestogen Replacement Therapy Does Not Adversely Affect Coagulation, Obstet. Gynecol., vol. 62, No. 5, pp. 596–600 (Nov. 1983) (P46).

Padwick, M.L. et al., Oestriol With Oestradiol Versus Oestradiol Alone: A Comparison of Endometrial, Symptomatic and Psychological Effects, British J. Obstet. Gynaecol., vol. 93, pp. 606–612 (Jun. 1986) (E28).

Physicians' Desk Reference 38th Ed., pp. 424, 1487–1495 (1984) (P29).

Rozenbaum, H., Progestatifs de Synthese et Metabolisme Lipidique, Contraception–Fertilite–Sexualite, Supp. vol. 12, No. 1, pp. 173–180 (1984) (P22).

Sipinen, S., Plasm Oestrone, Oestradiol and Gonadotrophin Concentrations in Postmenopausal Patients Treated With Oestradiol or With a Combination of Oestradiol and Oestriol, Annals of Clinical Research, vol. 11, pp. 172–178 (1979) (P3).

Sipinen, Seppo et al., Silastic Implants Releasing Estrone in the Treatment of Climacteric Complaints, Maturitas, vol. 2, pp. 213–224 (1980) (P35).

Socialstyrelsens Kommittee for Lakemedelsinformation (Health Board Committee on Medical Information), Menopaus, Substitutional Treatment with Estrogen, Workshop, Aug. 30–31, 1982, pp. 27, 30 (published 1983) [with translation] (Part of P2).

Socialstyrelsens Kommittee for Lakemedelsinformation (Health Board Committee on Medical Information), Menopaus, Substitutional Treatment with Estrogen, Workshop, Aug. 30–31, 1982, pp. 121, 161, 167–168 (published 1983) [with translation] (Part of P2).
Sporrong, T. et al., Comparison of Four Continuously Administered Progestogen Plus Oestradiol Combinations for Climacteric Complaints, British J. Obstet. Gynaecol., vol. 95, pp. 1042–1048 (Oct. 1988) (E12).
Staland, B., Continuous Treatment With a Combination of Estrogen and Gestagen—A way of Avoiding Endometrial Stimulation, Acta Obstet Gynecol Scand Suppl 130, pp. 29–35 (1985) (E29).
Staland, B., Treatment of Menopausal Oestrogen Deficiency Symptoms in Hysterectomised Women by Means of 17β–Oestradiol Pellet Implants, Acta. Obstet. Gynecol. Scand., vol. 57, pp. 281–285 (1978) (P18).
Stanczyk, Frank Z., Structure–Function Relationships, Potency, and Pharmacokinetics of Progestogens, in Treatment of Postmenopausal Women: Basic and Clinical Aspects, ch. 7, pp. 69–89 (Rogerio A. Lobo ed., 1994) (E26).
Sturdee, D.W. et al., Relations Between Bleeding Pattern, Endometrial Histology, and Oestrogen Treatment in Menopausal Women, Brit. Med. J., pp. 1575–1577 (Jun. 17, 1978) (P38).
Swyer, G.I.M., Potency of Progestogens in Oral Contraceptives—Further Delay of Menses Data, Contraception, vol. 26, No. 1, pp. 23–27 (Jul. 1982) (P19).
Swyer, G.I.M., Determination of Progestational Potency: A Review, J. Roy. Soc. Med., vol. 77, pp. 406–409 (1984) (P59).
Tausk, Marius, Pharmakologie der Hormone, pp. 83–87, 122–123 (1979) (P25).
Upton, Virginia G., Therapeutic Considerations in the Management fo Climacteric: A Critical Analysis of Prevalent Treatments, J. Reprod. Med., vol. 29, No. 2, pp. 71–80 (Feb. 1984) (P16).
Whitehead, M.I. et al., The Effects of Cyclical Oestrogen Therapy and Sequential Oestrogen/Progestogen Therapy on the Endometrium of Post–Menopausal Women, Acta Obstet. Gynecol. Scand, Suppl. 65, pp. 91–101 (1977) (P49).
Whitehead, M.I. & Campbell, S., Endometrial Histology, Uterine Bleeding and Oestrogen Levels in Menopausal Women Receiving Oestrogen Therapy and Oestrogen/Progestogen Therapy, Proceedings on the 2nd Int'l Meeting on Endometrial Cancer and Related Topics, pp. 65–80 (1978) (P50).
Whitehead, M.I. et al., Effects of Estrogens and Progestins on the Biochemistry and Morphology of the Postmenopausal Endometrium, New Eng. J. Med., vol. 305, No. 27, pp. 1599–1605 (Dec. 31, 1981) (P40).
Whitehead, M.I. et al., Actions of Progestins on the Morphology and Biochemistry of the Endometrium of Postmenopausal Women Receiving Low–Dose Estrogen Therapy, Am. J. Obstet. Gynecol., pp. 791–795 (Mar. 15, 1982) (P4).
Roger J.B. King, Aug. 29, 1995 (E25).
Curt Rune, Sep. 24, 1997 (E1 & E17).
Birgit Kronqvist, Sep. 17, 1997 (with translation) (E2).
Ruth Skoog, Feb. 3, 1997 (with translation) (E3).
Malcom Ian Whitehead, Oct. 15, 1997 (E22).
David W. Sturdee, Nov. 10, 1997 (E30).
Ove Heide–Jorgensen, Feb. 8, 1998 (with translation) (E31).
Ib Windfeld, Feb. 4, 1998 (with translation) (E32).
Bertil Staland, Nov. 24, 1997 (E33).
DUPHAR International Research B.V., Notice of Opposition to a European Patent, Oct. 21, 1997 (Party No. 04).
Novartis AG, Notice of Opposition to a European Patent, Oct. 20, 1997 (Party No. 03).
Novo Nordisk A/S, Notice of Opposition to a European Patent, Oct. 14, 1997 (Party No. 01).
Novo Nordisk A/S, Supplemental Notice of Opposition to a European Patent, Oct. 15, 1997 (Party No. 01).
Novo Nordisk A/S, Supplemental Notice of Opposition to a European Patent, Nov. 18, 1997 (Party No. 01).
Novo Nordisk A/S, Supplemental Notice of Opposition to a European Patent, Feb. 25, 1998 (Party No. 01).
Orion Pharma, Notice of Opposition to a European Patent, Oct. 22, 1997 (Party No. 10).
Ortho Pharmaceutical Corporation, Notice of Opposition to a European Patent, Oct. 22, 1997 (Party No. 07).
Pharmacia & Upjohn, Notice of Opposition to a European Patent, Oct. 21, 1997 (Party No. 06).
The Procter & Gamble Company, Notice of Opposition to a European Patent, Oct. 21, 1997 (Party No. 05).
R.P. Scherer Limited, Notice of Opposition to a European Patent, Oct. 17, 1997 (Party No. 02).
Schering AG, Notice of Opposition to a European Patent, Oct. 22, 1997 (Party No. 09).
Shire Pharmaceutical Contracts Limited, Notice of Opposition to a European Patent, Oct. 22, 1997 (Party No. 08).
Warner–Lambert Company, Notice of Opposition to a European Patent, Oct. 22, 1997 (Party No. 11).
Goretzlehner G. et al., Treatment of Menopausal Syndrome, Med. Akt., 8:418–419 (1982) (with English translation).
Kaiser, R., Hormonale Behandlung von Zyklusstorungen, 4th rev., p. 115 (1970).
McKay–Hart, D., A Comparative Trial of Kliogest With and Without Oestriol for the Prevention of Vasomotor Symptoms, Adverse Lipid Profile Changes and Oestoporosis in Postmenopausal Women (Dec. 15, 1993).
McKay–Hart, D., A Comparative Trial of Kliogest With and Without Oestriol Versus Cyclical Hormone Replacement Therapy in Treatment on Postmenopausal Women (Dec. 15, 1993).
Nishimo, Y. and Neumann, F., Sialic Acid Content in Mouse Female Reproductive Organs as a Quantitative Parameter for Testing the Estrogenicand Antiestrogenic Depot Effect, and Dissociated Effect of Estrogens on the Uterus and Vagina, Acta Endocrinologica (Copenhagen) Suppl., vol. 76 (187), p. 62 (1974) (Abstract).
Paterson, M.E.L. et al., Endometrial Disease After Treatment with Oestrogens and Progestogens in the Climacteric, Br. Med. J. vol. 280 (6217), pp. 822–824 (Mar. 22, 1980).
Physicians' Desk Reference 37th Ed., pp. 118, 405, 645–649 (1983).
Socialstyrelsens Kommittee for Lakemedelsinformation (Health Board Committee on Medical Information), Menopaus, Substitutional Treatment with Estrogen, Workshop, Aug. 30–31, 1982, pp. 1–164, 166 (published 1983).
Staland, B., Treatment of Climacteric Symptoms by Natural Oestrogens Without Stimulation of the Endometrium, Cancer Treatment Reports, vol. 63, No. 7, Abstr. No. 389 (Jul. 1979).
Whitehead, M.I., The Effects of Estrogens and Progestogens on the Postmenopausal Endometrium, Maturitas, vol. 1, No. 2, pp. 87–98 (1978) (Abstract).

Ylostalo, Perra et al., Serum Bile Acids and Lipids During Treatment of Climacteric Symptoms with Natural Estrogen–Progestin Combinations, Maturitas, vol. 3, No. 1, pp. 21–24 (1981).
SDM, Swedish Drug Market, I/1984 and II/1984.
Merck, p. 360 (1968).
Unlisted Drugs, vol. 22, No. 10, Oct. 1970, p. 149; Chatham, New Jersey, US; p. 149e: "Cyclo–Progynova".
Unlisted Drugs, vol. 25, No. 10, Oct. 1973, p. 160; Chatham, New Jersey, US; p. 160a: "Microgynon".
Unlisted Drugs, vol. 26, No. 11, Nov. 1974, p. 170; Chatham, New Jersey, US; p. 170b: "WL–20".
Unlisted Drugs, vol. 27, No. 8, Aug. 1975, p. 130; Chatham, New Jersey, US; p. 130g: "Nordiol".
Unlisted Drugs, vol. 28, No. 2, Feb. 1976, p. 20; Chatham, New Jersey, US; p. 26j: "Minidrill".
Unlisted Drugs, vol. 29, No. 3, Mar. 1977, p. 41; Chatham, New Jersey, US; p. 41g: "Adepal".
*Obstetrics and Gyneocology,* 63(6), 759–763 (Jun. 1984).

METHOD OF HORMONAL TREATMENT FOR MENOPAUSAL OR POST-MENOPAUSAL DISORDERS INVOLVING CONTINUOUS ADMINISTRATION OF PROGESTOGENS AND ESTROGENS

Matter enclosed in heavy brackets [ ] appears in the original patent but forms no part of this reissue specification; matter printed in italics indicates the additions made by reissue.

This is a continuation-in-part of U.S. Ser. No. 520,834, filed Aug. 5, 1983, now abandoned.

This invention relates to a method of hormonal treatment for menopausal (including perimenopausal and post-menopausal) disorders in women, and particularly to a treatment involving the continuous administration of a progestogen in conjunction with an estrogen. The invention further relates to a pharmaceutical composition comprising selected dosage units of progestogen and estrogen. In another aspect, the invention is concerned with a regimen comprising the continuous administration of progestogen in conjunction with the cyclical administration of estrogen and to a multi-preparation pack containing selected dosage units of progestogen and estrogen and particularly adapted to such regimen.

Perimenopausal (i.e. over approximately forty years of age), menopausal and post-menopausal women frequently experience a large variety of conditions and disorders which have been attributed to estrogen deprivation due to ovarian failure. The duration of these disorders can be extremely variable, and include hot flushes which can be devastating in some women and very mild in others. Dryness of the vagina associated with susceptibility to minor infections, and frequently associated with discomfort during intercourse, is another symptom which may be directly related to the decrease is estrogen availability.

In a long-term sense, one of the most health-threatening aspects of the menopause is the loss of mineral from bone (osteoporosis) which produces a decrease in bone mass and generates a serious risk of fractures. For example, evidence exists that there is a six-fold increase in fractures in post-menopausal women as opposed to men of the same age (Garraway et al, Mayo Clinic Proceedings, 54, 701–707, 1979). These fractures, of course, carry a high complication rate among older people, a marked increase in disability and general morbidity, and certainly an increased risk of mortality.

Another serious health-threatening aspect of the menopause the impressive loss of protection against heart attacks which is enjoyed by younger women up to the age of 60, when compared to men of the same age. The steep increase in mean serum cholesterol concentration which occurs around the menopause (during the fourth and fifth decades) may contribute importantly to the progressive increase in death from ischemic heart disease in older women. In the eighth and ninth decades, the incidence of deaths from ischemic heart disease, approaches that of men (Havlik, R.J. and Manning-Feinleid, P.H. 1979, NIH Publication No. 79-1610, U.S. Department of HEW).

In addition to the above-mentioned major physical problems, some women experience a larger variety of other symptoms ranging from depression, isomnia, and nervousness, to symptoms of arthritis and so forth.

It is generally agreed that estrogen is the most effective agent for the control or prevention of menopausal flushes and vaginal atrophy. It is effective in retarding or preventing the appearance of clinical evidence of osteoporosis. In appropriate doses, when combined with dl-norgestrel (or laevo-norgestrel), a favourable effect upon blood lipids is also seen. Problems with estrogen therapy do exist, however, and have been widely explored and documented in the medical literature. The means by which estrogen has been administered, generally speaking, involves either the use of estrogen [along] *alone* or estrogen plus a progestogen.

Estrogen [along] *alone*, given in small doses on a continuous basis, is effective in most patients for the control of the above symptoms and problems associated therewith. However, although the vast majority of women taking continuous low-dose estrogen will not have bleeding for many months or even years, there is a distinct risk posed by this routine of silently (i.e. exhibiting no overt symptoms) developing "hyperplasia of the endometrium". This term refers, of course, to an overstimulation of the lining of the uterus which can become pre-malignant, coupled with the possibility that the patient will eventually develop cancer of the uterine lining even under such a low-dose regimen (Gusberg et al, Obstetrics and Gynaecology, 17, 397–412, 1961).

Estrogen [along] *alone* can also be given in cycles, usually 21–25 days on treatment and 5–7 days off treatment. Again, if small doses of estrogen are required to control the symptoms and it is used to this fashion, only about 10% of women will experience withdrawal bleeding between the cycles of actual treatment. However, one must again be concerned by the risk of developing endometrial hyperplasia and by the increased relative risk of developing cancer of the uterus (Research on the Menopause: Report of a W.H.O. Scientific Group, 53–68, 1981).

The addition of progestogen for the last 7–10 days of each estrogen cycle will virtually eliminate the concern about developing endometrial hyperplasia and probably reduce the risk of developing endometrial carcinoma below that of the untreated general population. However, withdrawal bleeding will occur regularly in this routine and this is highly unacceptable to most older women (Whitehead, Am. J. Obs/Gyn., 142,6, 791–795, 1982).

Still another routine for estrogen administration would involve a formulation such as those found in birth control pills which contain relatively small doses of estrogen over the full 20–21 day treatment cycle, plus very substantial doses of potent progestogens over the same period of time. This routine, of course, not only produces withdrawal bleeding on each cycle, but is further unacceptable because such formulations have been shown to carry an increased risk of developing arterial complications such as stroke or myocardial infaraction in older women about the age of 35–40. This is especially true if the individual is a smoker of cigarettes (Plunkett, Am. J. Obs/Gyn. 142, 6, 747–751, 1982).

Therapeutic regimens employing a progestogen along require relatively large doses in order to control hot flushes. Moreover, use of a progestogen alone does not prevent atrophy of the vaginal mucosa, although it may help to prevent osteoporosis. However, a progestogen administered in large doses, together with large amounts of a synthetic estrogen, induces changes in blood lipids which may promote arteriosclerotic changes and have been implicated in the appearance of strokes and myocardial infarction among women taking oral contraceptives in their later reproductive years, (Plunkett, supra).

The present invention provides a novel therapeutic method and composition involving the use of low dosage levels of estrogens and progestogens, which method is designed to avoid or minimize bleeding and prevent overstimulation of the lining of the uterus while producing favourable changes in blood lipids. In particular, the method involves continuous and uninterrupted administration of very small doses of a progestogen along with administration of an estrogen, the latter being cyclical, where required (for example, with perimenopausal women). The method specifically provides for treatment of menopausal or post-menopausal disorders in a women comprising either:

A. continuously and uninterruptedly administering a progestogen and an estrogen to said woman, or B. continuously and uninterruptedly administering a progestogen and cyclically administering an estrogen to said woman by repetitively using a dosage regimen comprising:

(i) administering said estrogen continuously for period of time between about 20 and about 120 days, followed by (ii) terminating administering said estrogen for a period of time between about 3 and about 7 days.

The term "perimenopausal" refers to women of approximately forty years of age and older, who have not yet definitely arrived at menopause but who are experiencing symptoms associated with menopause.

The term "continuous" as applied in the specification and the claims to "administration" means that the frequency of administration is at least once daily. Thus, administration, e.g. every other day or once every third day, is not "continuous" for purposes of this invention. Note, however, that the frequency of administration may be greater than once daily and still be "continuous", e.g. twice or even three times daily so long as the dosage level as specified herein is not exceeded.

The term "uninterrupted" means that there is no break in the treatment. Thus "continuous, uninterrupted administration" of a progestogen would mean that the progestogen is administered at least once daily essentially in perpetuity or until the entire treatment is ended. In this regard, it should be noted that "cyclical" administration means that there is a break in administration and that, therefore, by definition, cyclical administration cannot be "uninterrupted".

The term "dosage level" means the total amount of estrogen or progestogen administered per day. Thus, for example, the "continuous administration" of a progestogen to a women at a "dosage level" of 75 micrograms means that the women receives a total of 75 micrograms of progestogen on a daily basis, whether the progestogen is administered as a single 75 microgram dose or, e.g. three separate 25 microgram doses. It is noted that the most conventional means of continuously administering an estrogen or progestogen is as a single daily oral dose at the prescribed dosage level. Parenteral modes of administration, which provide a slow release of the progestogen, could be substituted for the oral route.

Thus, the invention realizes the objects of providing a therapeutic method allowing for the administration of an estrogen, controlling hot flushes, restoring the vaginal mucosa to a healthier state, preventing the development of the dimineralization of bones as well as preventing changes in lipids which predispose to cardiovascular disease, over long periods of treatment, which method does not, however, initiate bleeding or increase the risk of endometrial carcinoma.

In another aspect, the invention provides a pharmaceutical composition for hormonal treatment of menopausal or post-menopausal disorders in a woman, which comprises a dosage unit of a progestogen and a dosage unit of an estrogen for continuous administration wherein the units comprise a progestogen in the range of 0.025 to 30 mg and an estrogen in the range of 0.005 to 2.5 mg together with a pharmaceutically acceptable inert carrier.

The actual unit dosages are selected according to conventionally known methods, e.g. body weight of patient and biological activity of the hormones, with the ultimate goal of producing the desired result with the minimum quantities of hormones.

The interruption of the estrogen administration is required in perimenopausal women to maintain normal periods and may be required in certain jurisdictions due to health concerns—particularly overstimulation of the lining of the uterus to cause a pre-malignant condition. The absence of estrogen for a short period allows the lining of the uterus to be sloughed and any pre-malignancy thus avoided. However, the inventors believe that even with continuous administration of estrogen, the presence of progestogen will give rise to sufficient atrification of the uterus that no such condition would be likely to occur.

A further and important object of the invention is to provide the means whereby a woman may receive the proper quantities and dosage units of the progestogen and estrogen for adherence to the prescribed regimen wherein the dosage of estrogen is cyclically administered. Such means takes the form of a multi-preparation pack, which facilitates administration by a nurse or physical in appropriate circumstances or, more usually, self-administration by the woman.

The multi-preparation pack contains sufficient dosage units of progestogen and estrogen for continuous administration of both said progestogen and said estrogen for a period of from about 20 to 120 days plus an additional number of dosage units of progestogen for administration for an additional period of time of from about 3 to about 7 days during which administration of said estrogen is terminated.

The estrogen used in the present disclosure may be those which are orally active and are suitable for oral contraception and selected from natural estrogens such as estradiol, estradiol-17β, estradiol valerate, conjugated equine estrogens, piperazine estrone sulphate, estrone, estriol, estriol succinate and polyestriol phosphate, or from synthetic estrogens such as ethinyl estradiol, quinestranol and mestranol. The natural estrogens are preferred.

The progestogen is again selected from those which are orally active and suitable for oral contraceptives and may be, [foro] *for* example, dl-norgestrel, laevo-norgestrel, norethindrone (norethisterone), norethindrone acetate, ethynodiol diacetate, medroxyprogesterone acetate, cyproterone acetate or norethynodrel.

In the following Tables 1A and 1B are listed preferred unit dosages, minimum unit dosages and maximum unit dosages for the estrogens and progestogens useful in this invention. The quantities are determined by the biological activities of the particular substances as obtained commercially from sources that normally supply them in micronized form.

TABLE 1A

ESTROGENS

| | Preferred | Dosage Minimum | (mg/day) Maximum |
|---|---|---|---|
| Natural estrogens (steroids) | | | |
| Estradiol | 1 | 0.500 | 2 |
| Estradiol-17β | 1 | 0.500 | 2 |
| Estradiol valerate | 1 | 0.500 | 2 |
| Conjugated equine estrogens | 0.600 | 0.300 | 2.5 |
| Estrene | 0.600 | 0.300 | 2.5 |

TABLE 1A-continued

| ESTROGENS | Preferred | Dosage Minimum | (mg/day) Maximum |
|---|---|---|---|
| Piperazine estrone sulphate (estropipate) | 0.500 | 0.250 | 2.5 |
| Estriol* | 0.100 | 0.050 | 0.500 |
| Estriol succinate* | 0.100 | 0.050 | 0.500 |
| Polyestriol phosphate* | 0.100 | 0.050 | 0.500 |
| Synthetic estrogens (steroids) | | | |
| Ethinyl estradiol | 0.010 | 0.005 | 0.020 |
| Mestranol | 0.015 | 0.005 | 0.040 |
| [Quinestranol] *Quinestrol* | 0.010 | 0.005 | 0.030 |

It may be noted that of the estrogens of Table 1A, the estriol preparations marked with an asterisk (*) have lower preference than estradiols or estrones because they fail to spare bone in post-menopausal women. However, they could be combined with natural or synthetic estrogens for the purpose of the invention. Also, it is preferable that the following non-steroidal estrogens—although useful in this invention—be avoided for women who have not definitely arrived at menopause (who could become pregnant)—estrogens of this type being known to induce vaginal cancer and other abnormalities in offspring if taken during the pregnancy:

| | | | |
|---|---|---|---|
| Stilboestrol | 0.100 | 0.020 | 2 |
| Stilboestrol dipropionate | 0.100 | 0.020 | 2 |
| Diethylstilboestrol | 1 | 0.400 | 2.5 |
| Chlorotrianiscos | 2 | 1 | 2.5 |
| Benzoestrol | 2 | 0.5 | 2.5 |
| Dienoestrol | 0.500 | 0.200 | 2.5 |
| Hexoestrol | 0.500 | 0.200 | 2.5 |
| Methallenoestril | 1 | 0.500 | 2.5 |

TABLE 1B

| PROGESTOGENS | Preferred | Dosage Minimum | (mg/day) Maximum |
|---|---|---|---|
| Laevo-norgestrel | 0.050 | 0.025 | 0.075 |
| dl-norgestrel | 0.100 | 0.050 | 0.150 |
| Norethindrone (norethisterone) | 0.30 | 0.15 | 1.0 |
| Norethindrone (norethisterone) acetate | 0.20 | 0.10 | 1.0 |
| Dydrogesterone | 10 | 5 | 30 |
| Medroxyprogesterone acetate | 2.5 | 1 | 15. |
| Norethynodrel | 1 | 0.200 | 5 |
| Allylestrenol | 2 | 1 | 30 |
| Lynoestrenol | 0.200 | 0.100 | 2 |
| Quingestanol acetate | 0.200 | 0.050 | 1 |
| Medrogestone | 2 | 1 | 10 |
| Norgestrienone | 0.050 | 0.020 | 0.200 |
| Dimethisterone | 1 | 0.500 | 15 |
| Ethisterone | 2.5 | 1 | 25 |
| Cyproterone acetate | 0.500 | 0.100 | 10 |
| Chlormadinone acetate | 0.300 | 0.100 | 1 |
| Megestrol acetate | 1 | 0.100 | 10 |

Although chlormadinone acetate and megestrol are useful in the context of this invention, it has been speculated that these progestogens may pre-dispose breast tumors, although no clinical proof exists to that effect. However, unless and until such suspicions are proven to be without foundation, these compounds are clearly of lower preference.

The estrogen/progestogen combinations may be administered non-orally by implants or intramuscular injections. Generally speaking, the required dosages are based upon somewhat lower daily dosage levels that those required for the orally administered estrogens and progestogens, for the simple reason that the former are directly released into the bloodstream with consequently greater activity than the same compounds when orally ingested.

Estradiol, estradiol valerate and estradiol 17-β are suitable candidates for estrogen implants, in maximum and minimum amounts of 100 mg and 20 mg, with 100 mg preferred. These quantities will be suitable for slow-release implants intended for replacement every 3 to 12 months.

Suitable progestogen implants and intramuscular injections are set forth in Table 1C.

TABLE 1C

| | Period | Total Quantity (mg) Preferred | Minimum | Maximum |
|---|---|---|---|---|
| Progestogen implants | | | | |
| Loevonorgestrel | every 2–5 yr. | 50 | 25 | 100 |
| dl-norgestrel | every 2–5 yr. | 100 | 50 | 200 |
| Norgestrienone | every 1–2 yr. | 100 | 25 | 200 |
| Norethindrone acetate | every 2–4 mon. | 100 | 25 | 200 |
| Intramuscular progestogen depots | | | | |
| Medroxyprogesterone acetate | every 3 mon. | 150 | 50 | 500 |
| Norethindrone enanthate | every 3 mon. | 50 | 20 | 400 |
| Gestrocol hexanoate | every 3 mon. | 100 | 50 | 400 |
| Algestone acetophenide | monthly | 50 | 20 | 300 |
| Hydroxyprogesterone hexanoate | weekly | 100 | 50 | 250 |
| Hydroxyprogesterone caproate | bi-weekly | 100 | 50 | 250 |

dl-Norgestrel, laevo norgestrel (the common name for d-13β-ethyl-17α-ethinyl-17β-hydroxygon-4-en-3-one), norethindrone (common name for 17-hydroxy-19-nor-17α-pregn-4-en-20-yn-3-one), ethynodiol diacetate (common name for 19-nor-17α-pregn-4-en-20-yne-3β, 17-diol diacetate), norethindrone acetate, and cyproterone acetate may also be administered by injection. It will be readily appreciated by those skilled in the art thay any other synthetic progestogen which is orally active or effective for use in conjunction with contraception is also suitable for use in this invention.

Any of the suitable estrogens and progestogens (particularly those listed in the foregoing tables) may be combined with one another in the quantities recited to give estrogen/progestogen combinations within the purview of the invention. Especially preferred combinations are those containing the estradiols or conjugated equine estrogens and the norgestrels norethindrones, or medroxyprogesterones. Thus, especially preferred combinations are:

Estradiol/Laevo-norgestrel
Estradiol 17β/Laevo-norgestrel
Estradiol valerate/Laevo-norgestrel
Conjugated equine estrogens/Laevo-norgestrel
Estradiol/dl-norgestrel
Estradiol 17β/dl-norgestrel
Estradiol valerate/dl-norgestrel
Conjugated equine estrogens/dl-norgestrel
Estradiol/Norethindrone (norethisteron)
Estradiol 17β/Norethindrone (norethisterone)
Estradiol valerate/Norethindrone (norethisterone)
Conjugated equine estrogens/Norethindrone (norethisterone)

Estradiol/Norethindrone (norethisterone) acetate

Estradiol 17β/Norethindrone (norethisterone) acetate

Estradiol valerate/Norethindrone (norethisterone) acetate

Conjugated equine estrogen/Norethindrone (norethisterone) acetate

Estradiol/Medroxyprogesterone acetate

Estradiol 17β/Medroxyprogesterone acetate

Estradiol valerate/medroxyprogesterone acetate

Conjugated equine estrogen/Medroxyprogesterone acetate

The maximum, minimum and preferred dosage levels for the respective estrogens and progestogens in the foregoing combinations are as recited in the tables.

The comparison of the invention is usually administered orally in admixture with a pharmaceutically acceptable inert carrier. The estrogen and progestogen can be compounded in any pharmaceutically acceptable inert (non-toxic) form. The packaging can be any system convenient for proper delivery. With the preferred orally administrable form, the pharmaceutical carrier can be of any of the conventionally employed carriers, for example pharmaceutically grades of mannitol, lactose, starch, magnesium stearate, sodium saccharin, talcum cellulose, glucose, sucrose, magnesium carbonate, and similar substances. The compositions may be formulated into solutions, suspensions, tablets, pills, capsules, powders, sustained release formulations, etc.

One of the unique aspects of this invention is the adaptation of the multi-preparation pact to the continuous uninterrupted administration of a progestogen and an estrogen is administered in a cyclic fashion. The duration of the estrogen cycle can be very variable, with continuous administration ranging between 20 and 120 days followed by a break (i.e. interruption) in estrogen administration ranging anywhere from about 3 to about 7 days. However, if the estrogen is discontinued for a period longer than 5 days, recurrence of hot flushes is most likely to occur, in a number of patients.

The multi-pack dispensing system may be accommodated by conventional packaging equipment, e.g. transparent strip foil packages continuously arranged in daily dosages or other conventional means in the art. Where the multi-pack is employed for the cyclical administration of an estrogen in combination with a progestogen, the pack would conveniently comprise a transparent strip foil package with the combined unit daily dosages arranged continuously with, for example, up to a total of 120 such dosages, the 3 to 7 unit dosages of progestogen being located at the end of the combined daily unit dosages whereby they would be taken at the end of the series.

The inventors have been developed clinical evidence from this routine that the amounts of estrogen and progestogen required to control flushes, vaginal symptoms and associated subjective symptoms are very small. Preliminary metabolic responses of the subjects indicative favourable changes toward the lower blood lipid levels found in younger premenopausal women.

EXAMPLE 1

An experimental study of thirty women was instituted under a randomized double blind protocol with crossover and involved the administration of placebos, progestogen only, estrogen only and the combination of the continuous, uninterrupted progestogen/cyclic estrogen treatment. Treatment comprised administering each hormone and the combination as follows: (1) estrogen alone for two months; (2) progestogen alone for two months; (3) combination therapy using (1) and (2) for six months. Each period of administering a hormone of the combination was followed by a one month period of placebo (substance with no endocrine activity) administration. The estrogen was micronized 17β-estradiol administered at a daily dosage level of 1 milligram, while the progestogen was dl-norgestrel administered at a dosage level of 75 micrograms.

Of 30 women who have completed this study, 22, on the basis of their responses throughout the fourteen months of observation, selected the combination treatment and requested to continue it. This represents a high level of acceptability.

EXAMPLE 2

In a follow-up phase of observation, 17 subjects (with intact uterus) have completed a total of 125 lunar months of the combination therapy (continuous, uninterrupted administration of dl-norgestrel, cyclic administration of 17β-estradiol). None of the patients experienced "bleeding" which required protection. 1.6 percent of the cycles involved spotting requiring no protection. 98.4 percent of the cycles were completely clear.

The combination therapy has been associated with no evidence whatsoever of endometrial hyperplasia (overstimulation of the lining of the uterus). One patient, after the 2-month phase of taking estrogen only (in the double blind study) did show evidence not only of hyperplasia of the endometrium but also had a typical findings which could be interpreted as indicative of a premalignant change. Addition of the small (75 microgram) dosage level of progestogen (dl-norgestrel) for two weeks only followed by full dilatation and curettage revealed that the endometrium had become completely atrophic once again and a total reversal of the previous findings were noted.

As an alternative to dl-norgtestrol, laevo-norgestral may be used. Since the dl-norgestrol consists of equal parts of the dextro (inactive) and laevo (active) forms, only half the quantity of laevo-norgestrol is used with the same effect. Thus, if laevo-norgestrol is substituted for dl-norgestrol in the foregoing examples, the laevo-norgestrol dosage level is 37.5 micrograms.

At least five cases of young women who required removal of ovaries and uterus because of severe endometriosis have also been successfully treated by the above combination. These women rarely have total removal of the endometriotic tissue. It is important to treat these patients with estrogen replacement therapy to prevent the early appearance of bone demineralization (osteoporosis), elevation of cholesterol and triglycerides and to control sever hot flushes and vaginal atrophy. If patients such as these are treated with estrogen alone, they frequently develop recurrence of pain symptoms due to residual endometriosis being restimulated by the administered estrogen. Because the inventors' combination therapy tends to promote atrophy of the lining of the uterus (endometrium) no matter whether it is located normally within the uterus or in the endometriotic tissue in the pelvis, it is found that these patients tolerate the treatment very well and do not have a recurrence or reactive of their endometriosis. Furthermore, even small doses of estrogen in combination with the continuous progestogen routine is sufficient to control the severe hot flushes which such patients experience.

Thus this invention permits control of menopausal disorders including hot flushes and vaginal atrophy along with many of the subjective symptoms. Further, given that both components of the combination therapy are considered to be effective in retarding osteoporosis, long term therapy to prevent this disabling disease should be effective.

Additionally, the risk of developing endometrial (uterine) cancer from the combination therapy should, at a minimum, be reduced to the normal incidence of the general population as opposed to the increased risk which has in fact been demonstrated to occur using estrogen-only treatment. The inventors have in fact developed some evidence suggestive that the combination therapy reduces the risk of premalignant endometrial changes, which may reduce the risk of developing endometrial cancer. The reduction in bleeding or spotting in patients taking the combination therapy makes it much more desirable relative to known treatments, particularly to older women.

The following describes directions which may be applied to a multi-preparation pack specifically adapted to the cyclical administration of estrogen together with the continuous administration of progestogen in accordance with one embodiment of the invention:

ABOUT THESE TABLETS (The tablet set herein) is used to control menopausal symptoms. It is not a birth control pill and cannot be relied upon to prevent pregnancy.

Oral contraceptives should not be taken at the same time as these tablets and, if necessary, you should therefore ask your doctor about alternative means of mechanical protection.

When treatment is first started, tingling of the breasts slight nausea or occasional vaginal bleeding may occur—this should settle after a short time.

If you have any unusual symptoms, contact your doctor.

To be taken under medical supervision.

HOW TO USE THIS PACK

Whether you are menstrating regularly or not, take the first tablet on a day suitable to yourself until all the tablets have been consumed.

The last seven tablets of the different colour are to be taken only when all others have been consumed.

Alternatively, the foregoing instructions may be printed as a leaflet, and the package instruction modified as follows:

Before commencing treatment please read the enclosed instruction leaflet carefully. If you have any difficulties following the instructions please ask your doctor for assistance.

DIRECTIONS

To remove a tablet, press firmly with your thumb on the appropriate clear plastic bubble. This may be helped by holding the card so that your fingers surround the aluminum foil through which the tablet will emerge.

*BRIEF DESCRIPTION OF THE DRAWINGS*

A multi-preparation pack suitable for administration of tablets in accordance with the regimen described above is illustrated in FIGS. 1 and 2 of the drawings. A bubble pack 10 (which may be folded along the line 10a) is sold in a protective sleeve 11, upon the rear of which are printed the directions for use and salient facts concerning the tablets, as indicated at 12 in the drawing. When removed from the protective sleeve by the consumer, the bubble pack contains as many tablets as the number of days which the pack is intended to cover (in this example, one hundred and twenty days). Optionally, the individual bubble segments may be numbered from one to one hundred and twenty but it is important that the last few segments, which contains the progestogen-only tablets, be clearly distinguished from the remainder of these segments. In the present example, the segments 13 containing the first one hundred and thirteen tablets (combination progestogen/estrogen) are a light colour (for example, white) whilst the last seven segments 14, containing the progestogen-only tablets are a dark colour (red, for example). By following the directions on the sleeve and observing the colours on the bubble pack (and the "day numbers", if present) the consumer will take the combination tablets for the first one hundred and thirteen days and the progestogen tablets for the last seven days. Thereafter, a new package would be opened, whereby the cycle is repeated.

Although only a few exemplary embodiments of this invention have been described in detail above, those skilled in the art will readily appreciate that many modifications are possible in the exemplary embodiments without materially departing from the novel teachings and advantages of this invention.

Figure 2:
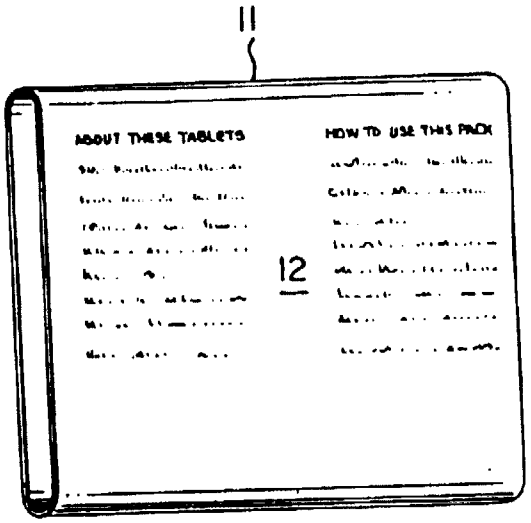
Figure 1:
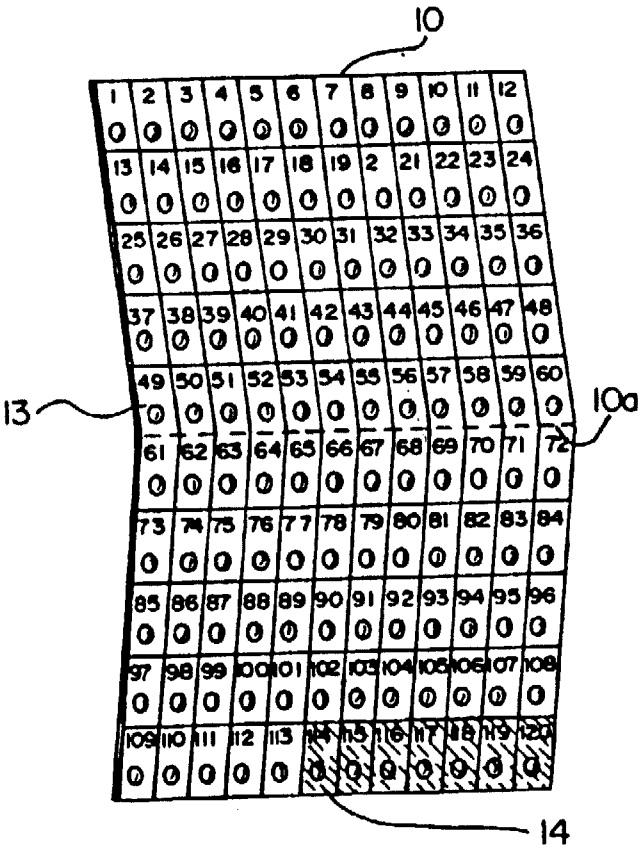

We claim:

[1. A method of hormonally treating menopausal or post-menopausal disorders in a woman, comprising administering to said woman continuously and uninterrupted both progestogen and estrogen in daily dosage units of progestogen equivalent to laevo-norgestrel dosages of from about 0.025 mg to about 0.075 mg, and of estrogen equivalent to estradiol dosages of about 0.5 mg to about 2.0 mg.]

[2. The method of claim 1 wherein said estrogen is 17 β-estradiol and said progestogen is dl-norgestrel or laevo-norgestrel, the daily dosage level of said 17 β-estradiol being about 1 mg, the daily dosage level of said dl-norgestrel (where present) being about 100 micrograms, and the daily dosage of said laevo-norgestrel (where present being about 50 micrograms.]

3. A method of hormonally treating perimenopausal, menopausal or post-menopausal disorders in a woman, comprising:

A. continuously and uninterruptedly administering a progestogen to said woman in daily dosage units of progestogen equivalent to laevo-norgestrel dosages of from about 0.025 mg to about 0.075 mg, and B. cyclically administering an estrogen to said woman by repetitively using a dosage regimen comprising:

(i) administering said estrogen continuously for a period of time between about 20 and about 120 days in daily dosage units of estrogen equivalent to estradiol dosages of from about 0.500 mg to about 2 mg, followed by (ii) terminating administering said estrogen for a period of time between about 3 and about 7 days.

4. The method of claim 3 wherein said progestogen is selected from the following group, with respective maximum and minimum daily dosage levels as follows:

| | Dosage (mg/day) Minimum | Maximum |
|---|---|---|
| Laeve-norgestrel | about 0.025 | about 0.075 |
| dl-norgestrel | about 0.050 | about 0.150 |
| Norethindrone (norethisterone) | about 0.15 | about 1.0 |
| Norethindrone (norethisterone) acetate | about 0.10 | about 1.0 |
| Ethynodiol diacetate | about 0.10 | about 1.0 |
| Dydrogesterone | about 5 | about 30 |
| Medroxyprogesterone acetate | about 1 | abou 15 |

-continued

| | Dosage Minimum | (mg/day) Maximum |
|---|---|---|
| Norethynodrel | about 0.203 | about 5 |
| Allylestrenol | about 1 | about 10 |
| Lynoestrenol | about 0.300 | about 2 |
| Quingestanol acetate | about 0.050 | about 1 |
| Medrogestone | about 1 | about 10 |
| Norgestrienone | about 0.020 | about 0.200 |
| Dimethisterone | about 0.500 | about 15 |
| Ethisterone | about 1 | about 25 |
| Cyproterone acetate | about 0.300 | about 10. |

5. The method of claim 3 wherein said estrogen is selected from the following group, with respective maximum and minimum daily dosage levels as follows:

| | Dosage Minimum | (mg/day) Maximum |
|---|---|---|
| Estradiol | about 0.500 | about 2 |
| Estradiol-17β | about 0.500 | about 2 |
| Estradiol valerate | about 0.500 | about 2 |
| Conjugated equine estrogens | about 0.300 | about 2.5 |
| Estrone | about 0.300 | about 2.5 |
| Piperazine estrone sulphate (estropipate) | about 0.250 | about 2.5 |
| Ethinyl estrodiol | about 0.005 | about 0.020 |
| Mestranol | about 0.005 | about 0.030 |
| [Quinestranol] *Quinestrol* | about 0.005 | about 0.020. |

6. The method of claim 5 or claim 4 wherein said estrogen is selected from the following group, with respective daily dosage levels as follows:

| | Dosage (mg/day) |
|---|---|
| Estradiol | about 1 |
| Estradiol-17β | about 1 |
| Estradiol valerate | about 1 |
| Conjugated equine estrogens | about 0.600 |
| Estrone | about 0.600 |
| Piperazine estrone sulphate (estropipate) | about 0.500 |
| Ethinyl estradiol | about 0.010 |
| Mestranol | about 0.015 |
| [Quinestranol] *Quinestrol* | about 0.010. |

7. The method of claim 5 wherein said progestogen is selected from the following group, with respective daily dosage levels as follows:

| | Dosage (mg/day) |
|---|---|
| Laevo-norgestrel | about 0.050 |
| dl-norgestrel | about 0.100 |
| Norethindrone (norethisterone) | about 0.30 |
| Norethindrone (norethisterone) | abour 0.30 |
| Ethynodiol diacetate | about 0.30 |
| Dydrogestrone | about 10 |
| Medroxyprogesterone acetate | about 2.5 |
| Norethynodrel | about 1 |
| Allylestrenol | about 2 |
| Lynoestrenol | about 0.200 |
| Quingestanol acetate | about 0.200 |
| Medrogestone | about 2 |
| Norgestrienone | about 0.050 |
| Dimethisterone | about 1 |
| Ethisterone | about 2.5. |

8. The method of [any of claims] *claim* 5 wherein said estrogen and said progestogen are selected from the following combination:

Estradiol/Laevo-norgestrel
Estradiol 17β/Laevo-norgestrel
Conjugated equine estrogens/Laevo-norgestrel
Estradiol/dl-norgestrel
Estradiol 17β/dl-norgestrel
Estradiol valerate/Laevonorgestrel
Estradiol valerate/dl-norgestrel
Conjugated equine estrogens/dl-norgestrel
Estradiol/Norethindrone (norethisteron)
Estradiol 17β/Norethindrone (norethisterone)
Estradiol valerate/Norethindrone (norethisterone)
Conjugated equine estrogens/Norethindrone (norethisterone)
Estradiol/Norethindrone (norethisterone) acetate
Estradiol 17β/Norethindrone (norethisterone) acetate
Estradiol valerate/Norethindrone (norethisterone) acetate
Conjugated equine estrogen/Norethindrone (norethisterone) acetate
Estradiol/Medroxyprogesterone acetate
Estradiol 17β/Medroxyprogesterone acetate
Estradiol valerate/Medroxyprogesterone acetate
Conjugated equine estrogen/Medroxyprogesterone acetate.

9. The method of claim 8 wherein said estrogen is 17β-estradiol and said progestogen is dl-norgestrel or laevo-norgestrel.

10. The method of claim 9 wherein the daily dosage level of said 17β-estradiol is between about 0.5 mg and about 2 mg, the daily dosage level of said dl-norgestrel, where present, is between about 50 and about 150 micrograms and the daily dosage level of said laevo-norgestrel, where present, is between about 25 and about 75 micrograms.

11. The method of claim 10 wherein the daily dosage level of said dl-norgestrel is about 75 micrograms.

[12. The method of claim 1 or 3 wherein said estrogen is a synthetic estrogen.]

[13. The method of claim 12 wherein said synthetic estrogen is selected from the group consisting of ethinyl estradiol, mestranol and quinestranol.]

[14. The method of claim 1 or 3 wherein said estrogen is a natural estrogen.]

[15. The method of claim 14 wherein said natural estrogen is selected from the group consisting of conjugated equine estrogens, estradiol, estradiol-17β estradiol valerate, estrone, piperazine estrone sulphate, estriol, estriol succinate and polyestrol phosphate.]

[16. The method of claim 1 or 3, wherein said progestogen is selected from the group consisting of laevo-norgestrel, dl-norge, trel, norethindrone (norethisterone), norethindrone (norethisteron) acetate, ethynodiol diacetate, dydrogesterone, medroxyprogesterone acetate, norethynodrel, allylestrenol, lynoestrenol, quingestanol acetate, medrogestone, norgestrienone, dimethisterone, ethisterone, and cyprotecone acetate.]

[17. A pharmaceutical composition for the hormonal treatment of perimenopausal, menopausal and post-menopausal disorders in a woman, said composition being in implantable or intramuscularly injectable form and comprising, in association with a pharmaceutically acceptable barrier, sufficient progestogen and estrogen to provide dosage levels to said woman equivalent to orally administered daily dosages of progestogen equivalent to laevo-norgestrel dosages of from about 0.025 mg to about 0.075 mg and of estrogen equivalent to estradiol dosages of about 0.5 mg to about 2 mg.]

[18. The pharmaceutical composition of claim 17 in implantable form, wherein said estrogen is selected from the group consisting of estradiol, estradiol-17β, and estradiol valerate.]

[19. The pharmaceutical composition of claim 18 or 17 in implantable form, wherein said progestogen is selected from the group consisting of laevo-norgestrel, dl-norgestrel, norgestrienone, and norethindrone acetate.]

[20. The pharmaceutical composition of claim 17 in injectable form, wherein said progestogen is selected from the group consisting of medroxyprogesterone acetate, norethindrone enanthate, gestronol hexanoate, and algestone acetophenide.]

*21. A method of hormonally treating menopausal or postmenopausal disorders in a woman to prevent or retard the demineralization of bone, comprising administering continuously and uninterruptedly over the treatment period, in fixed daily dosages and at dosages and a duration sufficient to effectively retard or prevent the demineralization of bone while minimizing spotting and/or bleeding, both progestogen and estrogen in daily dosage units of progestogen equivalent to laevo-norgestrel dosages of from about 0.025 mg to about 0.05 mg, and of estrogen equivalent to estradiol dosages of about 0.5 mg to about 2.0 mg.*

*22. A method of hormonally treating menopausal or postmenopausal disorders in a woman to prevent or retard the demineralization of bone, comprising administering continuously and uninterruptedly over the treatment period, in fixed daily dosages and at dosages and a duration sufficient to effectively retard or prevent the demineralization of bone while minimizing spotting and/or bleeding, both progestogen and estrogen in daily dosage units of progestogen equivalent to laevo-norgestrel dosages of from about 0.025 mg to about 0.075 mg, and of estrogen equivalent to estradiol dosages of about 0.5 mg to about 2.0 mg, wherein the progestogen and the estrogen are combined in a single dosage form.*

*23. A method of hormonally treating menopausal or postmenopausal disorders in a woman, comprising administering continuously and uninterruptedly over the treatment period, in fixed daily dosages which minimize spotting and/or bleeding, both progestogen and estrogen in daily dosage units of progestogen equivalent to laevo-norgestrel dosages of from about 0.025 mg to about 0.05 mg, and of estrogen equivalent to estradiol dosages of about 0.5 mg to about 0.25 mg.*

*24. A method of hormonally treating menopausal or postmenopausal disorders in a woman, comprising administering continuously and uninterruptedly over the treatment period, in fixed daily dosages which minimize spotting and/or bleeding, both progestogen and estrogen in daily dosage units of progestogen equivalent to laevo-norgestrel dosages of from about 0.025 mg to about 0.075 mg, and of estrogen equivalent to estradiol dosages of about 0.5 mg to about 2.0 mg, wherein the progestogen and the estrogen are combined in a single dose form.*

*25. The method of claim 21 or 23, wherein the progestogen and the estrogen are combined in a single dosage form.*

*26. The method of claim 21, 22, 23, 24 or 25, wherein the estrogen consists essentially of a bone-sparing estrogen.*

*27. The method of claim 21, 22, 23, 24 or 25, wherein the fixed daily dosages are administered over a treatment period of greater than 120 days.*

*28. The method of claim 21 or 22, wherein the dosages and duration of treatment are effective to prevent or retard osteoporosis.*

*29. The method of claim 21, 22, 23, 24 or 25, wherein the dosages and duration of treatment are sufficient to prevent or retard changes in blood lipids which might otherwise predispose the woman to cardiovascular disease.*

*30. The method of claim 21, 22, 23, 24 or 25, wherein said progestogen is selected from the group consisting of laevo-norgestrel, dl-norgestrel, ethynodiol diacetate, dydrogesterone, medroxyprogesterone acetate, norethynodrel, allylestrenol, lynoestrenol, quingestanol acetate, medrogestone, norgestrienone, dimethisterone, ethisterone, and cyproterone acetate.*

*31. The method of claim 22 or 24, wherein said progestogen is selected from the following group, with respective minimum and maximum daily dosage levels as follows:*

| | Dosage (mg/day) Minimum | Dosage (mg/day) Maximum |
|---|---|---|
| Laevo-norgestrel | about 0.025 | about 0.075 |
| dl-norgestrel | about 0.050 | about 0.150 |
| Ethynodiol diacetate | about 0.10 | about 1.0 |
| Dydrogesterone | about 5 | about 30 |
| Medroxyprogesterone acetate | about 1 | about 15 |
| Norethynodrel | about 0.200 | about 5 |
| Allylestrenol | about 1 | about 10 |
| Lynoestrenol | about 0.100 | about 2 |
| Quingestanol acetate | about 0.050 | about 1 |
| Medrogestone | about 1 | about 10 |
| Norgestrienone | about 0.020 | about 0.200 |
| Dimethisterone | about 0.500 | about 15 |
| Ethisterone | about 1 | about 25 |
| Cyproterone acetate | about 0.100 | about 10. |

*32. The method of claim 21, 23, 25, wherein said progestogen is selected from the following group, with respective minimum and maximum daily dosage levels as follows:*

| | Dosage (mg/day) Minimum | Dosage (mg/day) Maximum |
|---|---|---|
| Laevo-norgestrel | about 0.025 | about 0.050 |
| dl-norgestrel | about 0.050 | about 0.100 |
| Ethynodiol diacetate | about 0.10 | about 0.30 |
| Dydrogesterone | about 5 | about 10 |
| Medroxyprogesterone acetate | about 1 | about 2.5 |
| Norethynodrel | about 0.200 | about 1 |
| Allylestrenol | about 1 | about 2 |
| Lynoestrenol | about 0.100 | about 0.200 |
| Quingestanol acetate | about 0.050 | about 0.200 |
| Medrogestone | about 1 | about 2 |
| Norgestrienone | about 0.020 | about 0.050 |
| Dimethisterone | about 0.500 | about 1 |
| Ethisterone | about 1 | about 2.5 |
| Cyproterone acetate | about 0.100 | about 0.500. |

*33. The method of claim 21, 22, 23, 24 or 25, wherein said estrogen is selected from the group consisting of estradiol, estradiol-17β, conjugated equine estrogens, estradiol valerate, estrone, piperazine estrone sulphate, ethinyl estradiol, mestranol, and quinestrol.*

*34. The method of claim 33, wherein said estrogen is selected from the following group, with respective minimum and maximum daily dosage levels as follows:*

| | Dosage (mg/day) Minimum | Dosage (mg/day) Maximum |
|---|---|---|
| Estradiol | about 0.500 | about 2 |
| Estradiol-17β | about 0.500 | about 2 |

-continued

| | Dosage (mg/day) Minimum | Dosage (mg/day) Maximum |
|---|---|---|
| Estradiol valerate | about 0.500 | about 2 |
| Conjugated equine estrogens | about 0.300 | about 2.5 |
| Estrone | about 0.300 | about 2.5 |
| Piperazine estrone sulphate (estropipate) | about 0.250 | about 2.5 |
| Ethinyl estrodiol | about 0.005 | about 0.020 |
| Mestranol | about 0.005 | about 0.040 |
| Quinestrol | about 0.005 | about 0.030. |

35. The method of claim 34, wherein said estrogen is selected from the following group, with respective minimum and maximum daily dosage levels as follows:

| | Dosage (mg/day) Minimum | Dosage (mg/day) Maximum |
|---|---|---|
| Estradiol | about 0.500 | about 1 |
| Estradiol-17β | about 0.500 | about 1 |
| Estradiol valerate | about 0.500 | about 1 |
| Conjugated equine estrogens | about 0.300 | about 0.600 |
| Estrone | about 0.300 | about 0.600 |
| Piperazine estrone sulphate (estropipate) | about 0.250 | about 0.500 |
| Ethinyl estrodiol | about 0.005 | about 0.010 |
| Mestranol | about 0.005 | about 0.015 |
| Quinestrol | about 0.005 | about 0.010. |

36. The method of claim 30, 31, 32, 33, 34 or 35, wherein the fixed daily dosages are administered over a treatment period of greater than 120 days.

37. The method of claim 21, 23 or 25, wherein the progestogen is medroxyprogesterone acetate in an amount of from about 1 mg to about 2.5 mg.

38. The method of claim 21, 22, 23, 24 or 25, wherein the estrogen is conjugated equine estrogens in an amount of from about 0.300 mg to about 2.5 mg.

39. The method of claim 21, 23 or 25, wherein the progestogen is medroxyprogesterone acetate in an amount of from about 1 mg to about 2.5 mg, and the estrogen is conjugated equine estrogens in an amount of from about 0.300 mg to about 2.5 mg.

40. The method of claim 39, wherein the estrogen is conjugated equine estrogens in an amount of from about 0.300 to about 0.600.

41. The method of claim 39, wherein the progestogen is medroxyprogesterone acetate in an amount of about 2.5 mg and the estrogen is conjugated equine estrogens in an amount of about 0.600 mg.

42. The method of claim 39, wherein the progestogen is medroxyprogesterone acetate in an amount of about 2.5 mg and the estrogen is conjugated equine estrogens in an amount of about 0.300 mg.

43. The method of claim 37, 38, 39, 40, 41 or 42, wherein the fixed daily dosages are administered over a treatment period of greater than 120 days.

44. The method of claim 37, 38, 39, 40, 41 or 42, wherein the dosages and duration of treatment are sufficient to prevent or retard changes in blood lipids which might otherwise predispose the woman to cardiovascular disease.

45. The method of claim 21, 23 or 25, wherein said progestogen is norethindrone (norethisterone) acetate in an amount of from about 0.10 mg to about 0.20 mg.

46. The method of claim 21, 22, 23, 24 or 25, wherein said estrogen is selected from the group consisting of estradiol, estradiol 17-β, or estradiol valerate and is in an amount of from about 0.500 to about 1 mg.

47. The method of claims 22 or 24, wherein the estrogen is estradiol-17β administered in fixed daily dosages of between about 0.500 and about 1 mg and the progestogen is norethindrone acetate.

48. The method of claim 47, wherein the fixed daily dosages are administered over a treatment period of greater than 120 days.

49. The method of claim 47, wherein the dosages and duration of treatment are sufficient to prevent or retard changes in blood lipids which might otherwise predispose the woman to cardiovascular disease.

50. The method of claim 21, 23, 25 or 27, wherein said estrogen is piperazine estrone sulphate (estropipate).

51. The method of claim 21, 23, 25 or 27, wherein said estrogen is 17β-estradiol and said progestogen is dl-norgestrel or laevo-norgestrel, the daily dosage level of said 17β-estradiol being about 1 mg, the daily dosage level of said dl-norgestrel (where present) being about 100 micrograms, and the daily dosage of said laevo-norgestrel (where present) being about 50 micrograms.

52. The method of claim 21, 22, 23, 24 or 25 wherein the selected dosages are the minimum effective quantities of progestogen and estrogen.

53. The method of claim 21 or 23, wherein said daily dosages of progestogen and estrogen are administered once daily.

54. The method of claim 22, 24 or 25, wherein said single dosage form is a tablet.

55. The method of claim 21, 22, 23 or 24, wherein said progestogen is in micronized form.

56. The method of claim 21, 22, 23 or 24, wherein said estrogen is a synthetic estrogen.

57. The method of claim 21, 22, 23 or 24, wherein the estrogen is a natural estrogen.

* * * * *